(12) United States Patent
DeSilva et al.

(10) Patent No.: US 10,898,627 B2
(45) Date of Patent: Jan. 26, 2021

(54) VENTRICULAR ASSIST DEVICE

(71) Applicant: California Cardiac Solutions, Inc, Rancho Santa Margarita, CA (US)

(72) Inventors: Peter DeSilva, Rancho Santa Margarita, CA (US); Steve Smith, Trabuco Canyon, CA (US)

(73) Assignee: California Cardiac Solutions, Inc., Rancho Santa Margarita, CA (US)

( * ) Notice: Subject to any disclaimer, the term of this patent is extended or adjusted under 35 U.S.C. 154(b) by 118 days.

(21) Appl. No.: 16/132,304

(22) Filed: Sep. 14, 2018

(65) Prior Publication Data
US 2019/0143020 A1 May 16, 2019

Related U.S. Application Data

(63) Continuation-in-part of application No. 15/405,210, filed on Jan. 12, 2017, now Pat. No. 10,286,134.

(51) Int. Cl.
*A61M 1/12* (2006.01)
*A61M 1/10* (2006.01)

(52) U.S. Cl.
CPC .......... *A61M 1/122* (2014.02); *A61M 1/1008* (2014.02); *A61M 1/1013* (2014.02); *A61M 1/1086* (2013.01); *A61M 1/1068* (2013.01)

(58) Field of Classification Search
CPC .. A61M 1/122; A61M 1/1008; A61M 1/1013; A61M 1/1086; A61M 1/1068
USPC .......................................................... 600/16
See application file for complete search history.

(56) References Cited

U.S. PATENT DOCUMENTS

| | | | |
|---|---|---|---|
| 6,279,322 B1 * | 8/2001 | Moussa | F04D 29/444 60/751 |
| 2006/0122456 A1 * | 6/2006 | LaRose | A61M 1/1017 600/16 |

* cited by examiner

*Primary Examiner* — Amanda K Hulbert
*Assistant Examiner* — Philip C Edwards
(74) *Attorney, Agent, or Firm* — Roy Ekstrand

(57) ABSTRACT

A ventricular assist device for use in a human recipient includes a housing within which a series pair of turbine pump segments, each having a deswirler, are operative. The series pair of turbine pump segments provides a redundancy which in turn enhances the safety factor provided by the ventricular assist device.

4 Claims, 6 Drawing Sheets

VENTRICULAR ASSIST DEVICE

CROSS-REFERENCE TO RELATED APPLICATION

This application is a Continuation-In-Part of previously filed co-pending U.S. patent application Ser. No. 15/405,210 entitled VENTRICULAR ASSIST DEVICE, filed Jan. 12, 2017 in the names of Peter DeSilva and Steve Smith, the disclosure of which is incorporated herein by reference.

FIELD OF THE INVENTION

This invention relates generally to apparatus for sustaining and continuing life for patients having failing or failed hearts and particularly to artificial devices, known generally in the art as "Ventricular Assist Devices" (VADs), including ventricular assist devices such as "Left Ventricle Assist Devices" (LVADs) also used to supplement the performance of weak or failing hearts. This invention also further relates to U.S. Pat. No. 9,314,559, issued to Steve Smith and Peter DeSilva, entitled FOUR CHAMBER REDUNDANT-IMPELLER ARTIFICIAL HEART, the disclosure of which is hereby incorporated herein by reference.

BACKGROUND OF THE INVENTION

For many years, practitioners in the medical treatment and medical device arts have endeavored to provide artificial heart devices constructed to replace a failed or failing heart within a patient recipient. The most basic long term need is the creation of a replacement pumping device which is capable of performing the basic blood pumping and circulation functions of the natural heart.

Early attempts to provide a sustainable heart replacement were severely limited by the available technologies and the state of the art at that time. Devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses.

One of the more recent attempts to provide a reliable and practical artificial heart device which embodies great promise, is shown in the above-referenced and incorporated U.S. Pat. No. 9,314,559 which sets forth an artificial heart for use in a human recipient that includes a housing within which a quartet of turbine pump segments are operative. The quartet of turbine pump segments provides a redundancy which in turn enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

In a field of endeavor closely related to the attempts to provide a practical and reliable implantable artificial heart, practitioners have also been addressing the need for a ventricular assist device. Such ventricular assist devices (VADs) supplement the performance of a weakened heart without fully replacing it. Ventricular assist devices provide an implantable mechanical pump that helps blood flow from the lower chambers of a weakened heart, the ventricles, to other parts of the body or other parts of the heart itself. One of the most prevalent uses of such ventricular assist devices, known as a left ventricular assist device LVAD, is implanted in the patient's chest cavity and is used to pump blood from the lower portion of the left ventricle to the heart aorta.

A successful ventricular assist device must, above all, be long lasting and reliable. The dire consequences to the device recipient brought about by device failure make this requirement all too apparent. In addition, however, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stresses. Additional requirements such as avoidance of turbulence within the blood flow, blood cell damage by the pumping apparatus and the prevention of blood clot forming stagnation regions make further demands upon ventricular assist devices.

A substantial number of recently explored technologies attempting to provide successful implantable ventricular assist devices have chosen to utilize pumping apparatus which includes a rotating impeller such as a turban impeller or the like. While rotating turbine impeller type pumps have shown great promise for ventricular assist devices, a limitation has arisen which takes the form of rotational blood flow turbulence created by the rotating impellers of the turbine pumps. This turbulence has been found to exhibit vortex characteristics which are undesirable in application to blood pumping apparatus.

In a related art, various apparatus have been provided for reducing or mitigating the turbulence within fluid flow systems induced by the rotating pumps such as turbine pumps or the like. Such apparatus are often referred to in the art as "deswirlers" or "flow straighteners". Such devices are typically placed downstream in the fluid flow relative to the rotating pump elements with the object of counteracting the rotational turbulence component in the flow produced by the rotating pump elements. In one such element a type of "fluid collimator" is provided in which a plurality of generally small fluid passages are arranged in a parallel relationship much like a box of drinking straws. In another type of deswirler device, a plurality of vanes are situated within the fluid flow downstream of the rotating pump element.

Thus, while practitioners in the medical treatment and medical device arts have created a virtually endless number of proposed artificial ventricular assist devices, there remains nonetheless a continuing unresolved need in the art for an improved, implantable, reliable and effective artificial ventricular assist device which meets the stringent, unforgiving and vital requirements and challenges posed by a truly fully functioning completely implantable ventricular assist device.

SUMMARY OF THE INVENTION

Accordingly, it is a general object of the present invention to provide an artificial ventricular assist device which is reliable, implantable and effective. It is a more particular object of the present invention to provide an improved ventricular assist device which avoids the need for external component apparatus. It is a still more particular object of the present invention to provide an artificial ventricular assist device which eliminates, or substantially minimizes, rotational turbulence or vortex creation within the blood flow.

In accordance with the present invention, there is provided a ventricular assist device comprising: a housing having an input connector and an output connector, a first turbine pump operative to flow blood from the input connector to the output connector; a first deswirler located downstream of the first turbine pump; a second turbine pump operative to flow blood from the input connector to the output connector; a second deswirler located downstream of the second turbine pump wherein the first and second deswirlers are operative upon the blood flows from the first and second turbine pumps respectively to reduce or eliminate rotational turbulence or vortex blood flow due to the rotations of the turbine pump impellers.

From another perspective, the present invention provides a ventricular assist device comprising: a housing having an input, an output, a first turbine pump and first deswirler operative to flow blood from the input to the output; a second turbine pump and second deswirler also operative to flow blood from the input to the output. In a preferred fabrication of the present invention ventricular assist device, the first and second turbine pumps are arranged in series pairs within the blood flow. In one embodiment, the first and second turbine pumps and their respective deswirlers are operative within a curved generally U-shaped blood flow passage. In an alternate embodiment, the first and second turbine pumps and their respective deswirlers are supported within a housing defining a straight-line blood flow path.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS OF THE INVENTION

Figure 1:
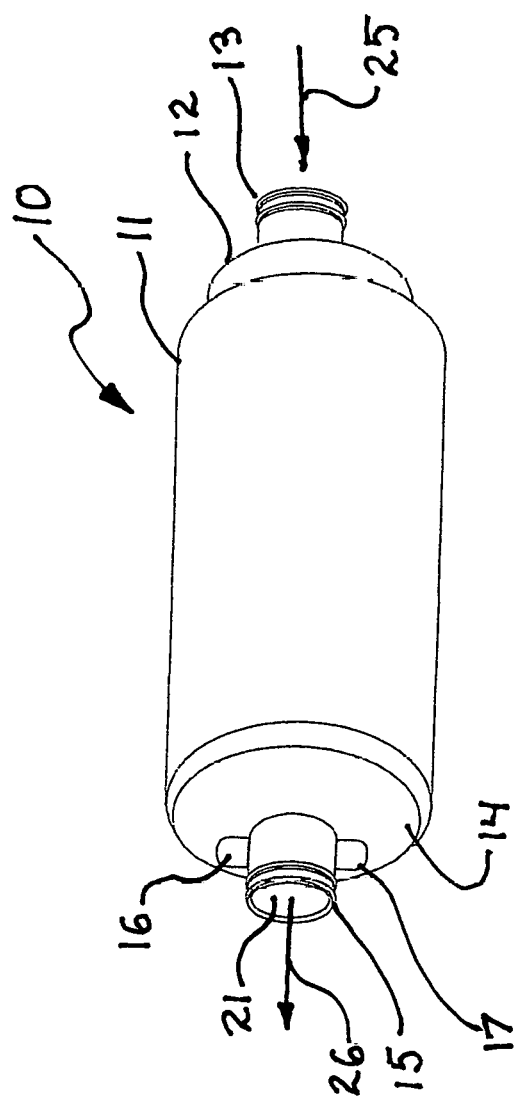
FIG. 1 sets forth a perspective view of a ventricular assist device constructed in accordance with the present invention.

FIG. 1 sets forth a perspective view of a ventricular assist device constructed in accordance with the present invention and generally referenced by numeral 10. Ventricular assist device 10 is generally cylindrical in shape and thus includes a cylindrical housing 11 supporting end caps 12 and 14 at each end thereof. End cap 12 further supports an input coupler 13 defining an input passage 20 (better seen in FIG. 2) while end cap 14 further supports an output coupler 15 defining an output passage 21 therethrough. Output coupler 15 further supports a pair of flow sensors 16 and 17.

In operation, ventricular assist device 10 is operative really coupled to a power and control system in the manner set forth and described in the above incorporated co-pending patent application. Suffice it to note here that as set forth below in greater detail ventricular assist device 10 includes a pair of turbine pumps 30 and 50 (seen in FIG. 3) which operate to draw blood into input coupler 13 in the direction indicated by arrow 25 and pump it at increased pressure outwardly through output coupler 15 in the direction indicated by arrow 26. Flow sensors 16 and 17 operate to sense the blood flow outwardly through output passage 21 for monitoring performance of ventricular assist device 10 in the manner also described in the above in the above incorporated co-pending patent application.

Figure 2:
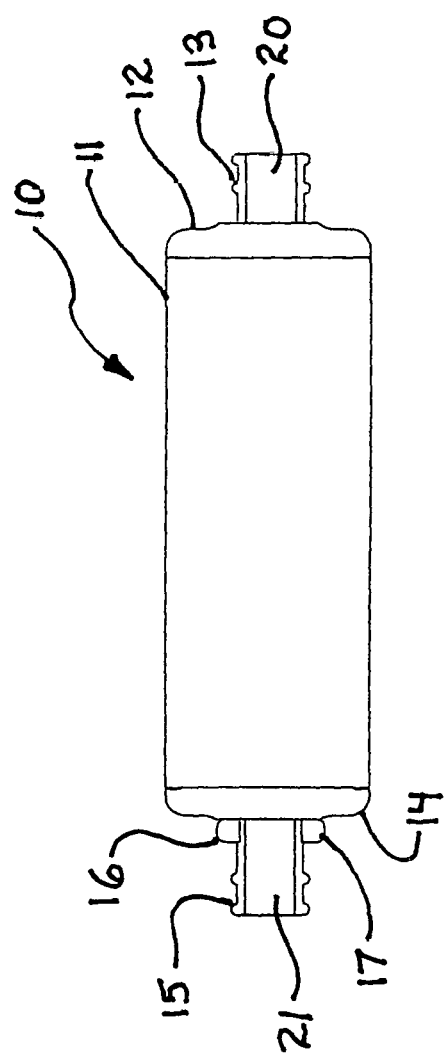
FIG. 2 sets forth a side elevation view of a ventricular assist device constructed in accordance with the present invention.

FIG. 2 sets forth a side elevation view of ventricular assist device 10. As described above, ventricular assist device 10 includes a generally cylindrical housing 11 supporting end caps 12 and 14 which in turn support an input coupler 13 and output coupler 15. The latter supports a pair of flow sensors 16 and 17. Input coupler 13 defines an input passage 20 while output coupler 15 defines an output passage 21. While not shown in FIG. 2, it will be understood that in a typical application, ventricular assist device 10 is coupled to a blood circulatory system within a host patient by suitable blood vessel connections to input coupler 13 and output coupler 15.

Figure 3:
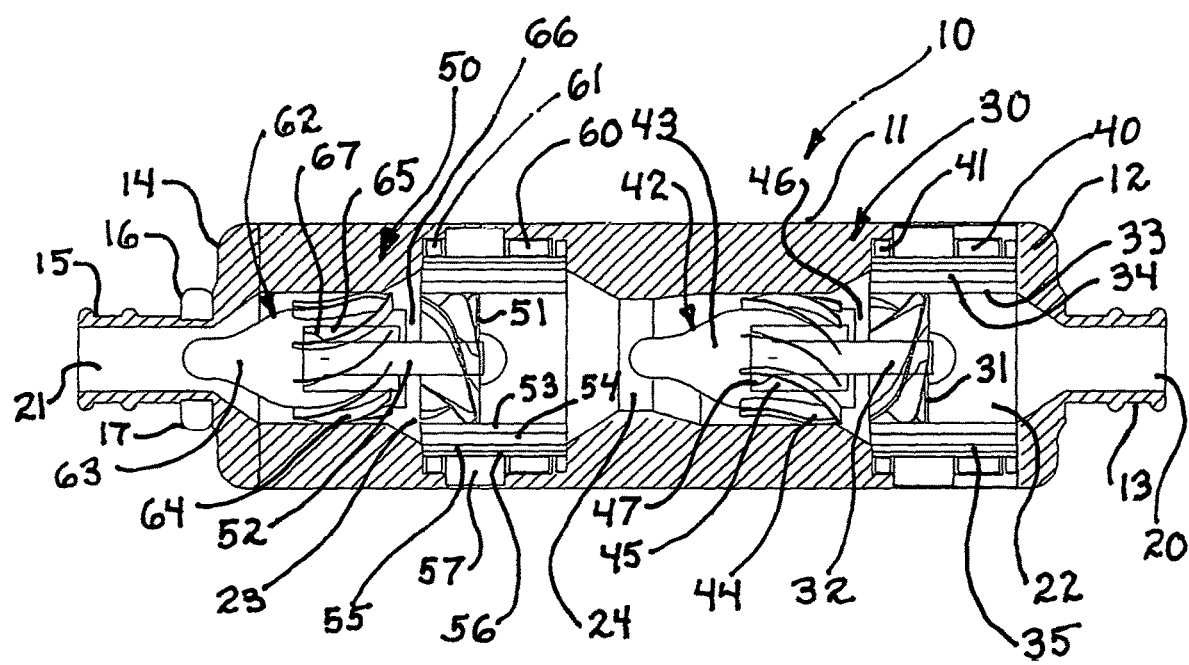
FIG. 3 sets forth a section view of a ventricular assist device constructed in accordance with the present invention.

FIG. 3 sets forth a section view of ventricular assist device 10. As described above ventricular assist device 10 includes a generally cylindrical housing 11 supporting a pair of and caps 12 and 14. End caps 12 and 14 support an input coupler 13 and an output coupler 15 respectively. Input coupler 13 further defines an input passage 20 extending through input coupler 13 and end 12. Correspondingly, output coupler 15 defines an output passage 21 extending through output coupler 15 and end cap 14. Housing 11 further defines a pump receptacle 22 within which a turbine pump 30 is supported. Housing 11 further defines a pump receptacle 23 within which a turbine pump 50 is supported. Pump receptacles 22 and 23 are coupled by a Venturi passage 24 such that a continuous blood flow passage between input passage 20 of input coupler 13 and output passage 21 of output coupler 15 is formed.

Turbine pump 30 includes a turbine impeller 31 supported upon an arbor 32. Turbine pump 30 further includes a generally cylindrical rotor 33 which is joined to the outer edges of turbine impeller 31 and is therefore rotatable therewith. A cylindrical isolator 35 is preferably formed of a suitable glass material and is fixed to the interior of pump receptacle 22 of housing 11. Isolator 35 is spaced from rotor 33 such that an air gap 34 is formed between rotor 33 and isolator 35. A motor core 36 encloses isolator 35 and is similarly fixed within pump receptacle 22. Turbine pump 30 further includes an outer core ring 37 encircling the outer surface of motor core 36. Turbine pump 30 further includes windings 40 and 41 on either side of outer core ring 37 which similarly encircle motor core 36.

Turbine pump 30 further includes a deswirler 42 having a deswirler body 43 which supports a plurality of curved deswirler vanes 44. Deswirler vanes 44 extend from deswirler body 43 and are fixed within the interior of Venturi passage 24 of housing 11 and secure the position of deswirler 42 therein. Deswirler body 43 further supports a bushing 45 which in turn receives the remaining end of arbor 32. A flared portion 47 is formed between the end of arbor 32 and the end of bushing 45 to provide a thrust load carrying surface which maintains arbor 32 within bushing 45. Arbor 32 is rotatable within bushing 45 such that a bearing is formed therebetween. In the preferred fabrication of the present invention, arbor 32 and bushing 45 are made of a jewel bearing material such as sapphire, or the like.

Turbine pump 50 is virtually identical to turbine pump 30 and thus includes a turbine impeller 51 supported upon an arbor 52. Turbine pump 50 further includes a generally cylindrical rotor 53 which is joined to the outer edges of turbine impeller 51 and is therefore rotatable therewith. A cylindrical isolator 55 is preferably formed of a suitable glass material and is fixed to the interior of pump receptacle 23 of housing 11. Isolator 55 is spaced from rotor 53 such that an air gap 54 is formed between rotor 53 and isolator 55. A motor core 56 encloses isolator 55 and is similarly fixed within pump receptacle 23. Turbine pump 50 further includes an outer core ring 57 encircling the outer surface of motor core 56. Turbine pump 50 further includes windings 60 and 61 on either side of outer core ring 57 which similarly encircle motor core 56.

Turbine pump 50 further includes a deswirler 62 having a deswirler body 63 which supports a plurality of curved deswirler vanes 64. Deswirler vanes 64 extend from deswirler body 63 and are fixed within the interior of pump receptacle 23 of housing 11 and secure the position of deswirler 62 therein. Deswirler body 63 further supports a bushing 65 which in turn receives the remaining end of arbor 52. A flared portion 67 is formed between the end of arbor 52 and the end of bushing 65 to provide a thrust load carrying surface which maintains arbor 52 within bushing 65. Arbor 52 is rotatable within bushing 65 such that a bearing is formed therebetween. In the preferred fabrication of the present invention, arbor 52 and bushing 65 are made of a jewel bearing material such as sapphire, or the like.

In operation, ventricular assist device 10 is positioned within a patient's circulatory system in the manner described in the above-referenced incorporated co-pending patent application utilizing suitable connecting apparatus (not shown) for securing input coupler 13 and output coupler 15 to the patient's blood vessels. As is also described in the above-referenced incorporated co-pending patent application, a power and control system (not shown) is operatively coupled to the electric motor windings within turbine pumps 30 and 50 to provide energizing and control signals for operation of the electric motors therein. As turbine impellers 31 and 51 are caused to rotate, a flow of blood is induced which flows into input passage 20 of input coupler 13 and thereafter through turbine impeller 31 and deswirler 42 through Venturi passage 24 and into pump receptacle 23. This flow continues increased by the rotation of turbine impeller 51 and the resulting blood flow continues outwardly from pump receptacle 23 past deswirler 62 exiting through output passage 21 of output coupler 15. In accordance with an important aspect of the present invention the blood flows induced by the rotations of turbine impellers 31 and 51 immediately flows through the structures of deswirlers 42 and 62 respectively. It will be noted that deswirler vanes 44 of deswirler 42 are oppositely curved with respect to the vanes of turbine impeller 31. This relationship allows deswirler 42 to overcome or straighten the rotational vortex turbulence induced within the blood low as turbine impeller 31 is rotated. This operation is often referred to in the art as "flow straightening". As a result the blood flow leaving deswirler 42 and entering Venturi passage 24 is substantially free of rotational vortex turbulence. A similar oppositely curved relationship exists between deswirler vanes 64 and turbine impeller 51. Accordingly, deswirler 62 is similarly operative to ensure that the outward blood flow through output passage 21 of output coupler 15 is also substantially free of rotational vortex turbulence.

It has been determined that the size of gap 46 between turbine impeller 31 and deswirler 42 and the size of gap 66 between turbine impeller 51 and deswirler 62 are critical to the proper operation of flow straightening. Accordingly, gaps 46 and 66 are preferably maintained at 0.5 millimeters.

It will be noted that ventricular assist device 10 is shown having a pair of redundant turbine pump and deswirler stages. It will be recalled that this greatly increases the reliability of the ventricular assist device. It will also be apparent to those skilled in the art that redundance may be further enhanced by using a greater plurality of turbine pump and deswirler stages, such as three or four or more, without departing from the spirit and scope of the present invention.

Figure 4:
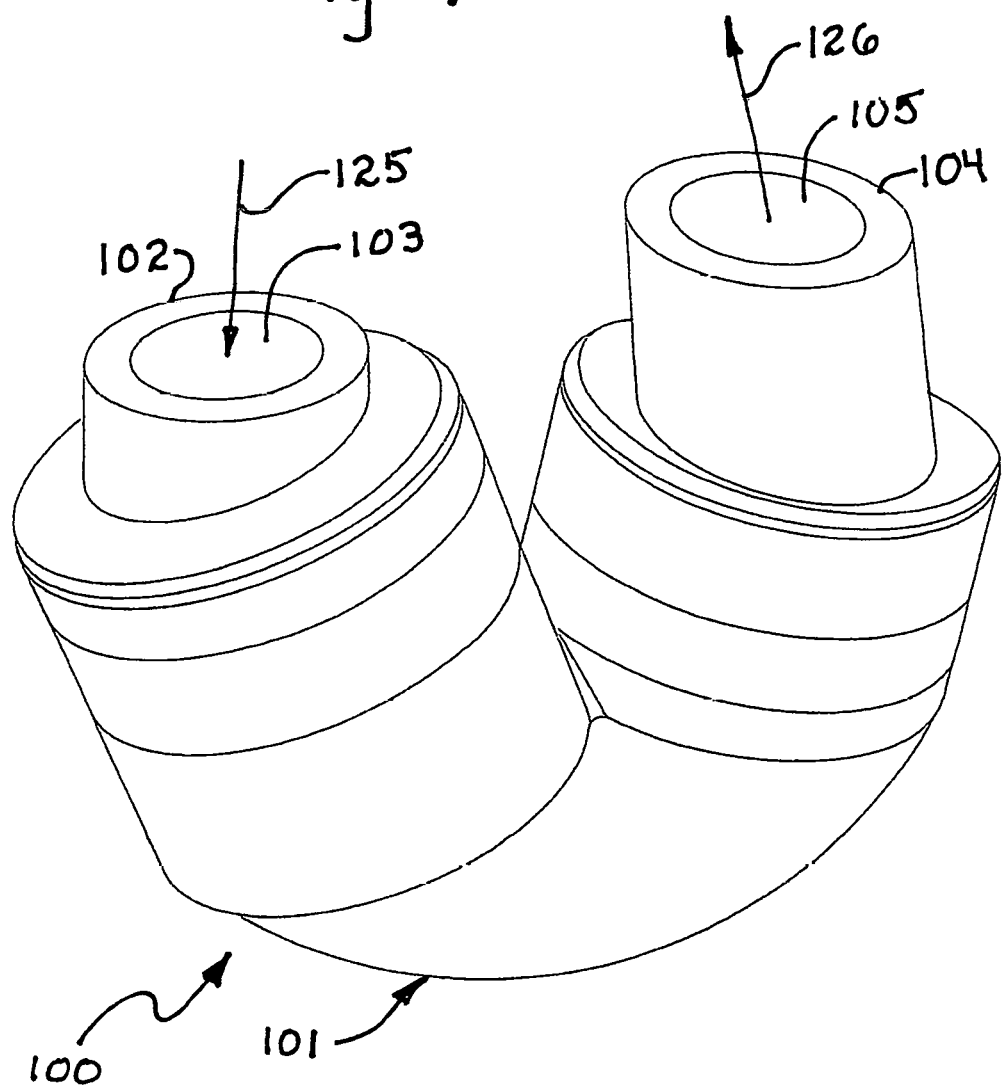
FIG. 4 sets a perspective view of an alternate embodiment of the present invention ventricular assist device.

FIG. 4 sets forth a perspective view of an alternate embodiment of the present invention ventricular assist device constructed to maintain the input and output connections facing in a common direction generally referenced by numeral 100. Ventricular assist device 100 is generally U-shaped and includes a U-shaped housing 101 supporting an input coupler 102 defining an input passage 103 and an output coupler 104 defining an output passage 105.

In operation, ventricular assist device 100 is operative really coupled to a power and control system in the manner set forth and described in the above incorporated co-pending patent application. Suffice it to note here that as set forth below in greater detail ventricular assist device 100 includes a pair of turbine pumps 130 and 150 (seen in FIG. 6) which operate to draw blood into input coupler 102 in the direction indicated by arrow 125 and pump it at increased pressure outwardly through output coupler 104 in the direction indicated by arrow 126.

Figure 5:
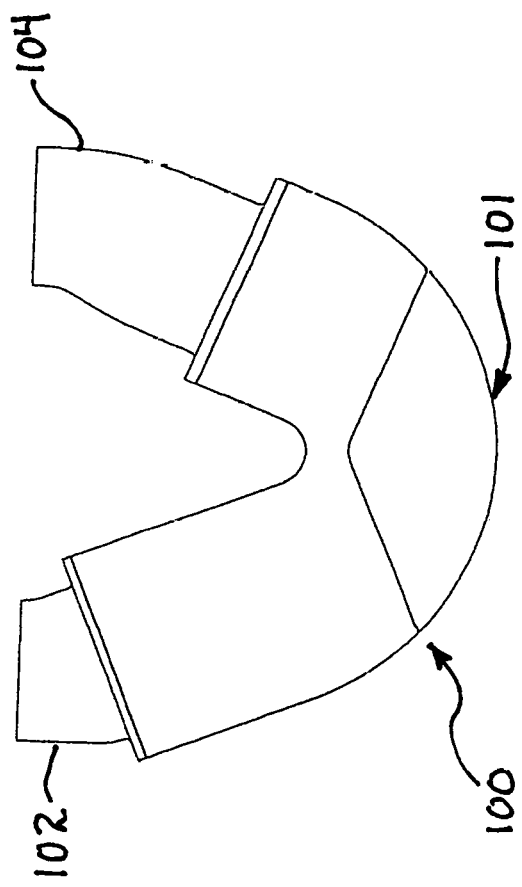
FIG. 5 sets forth a side elevation view of the alternate embodiment of the present invention ventricular assist device set forth in FIG. 4.

FIG. 5 sets forth a side elevation view of ventricular assist device 100. As described above, ventricular assist device 100 includes a generally U-shaped housing 101 supporting and input coupler 102 and output coupler 104. While not shown in FIG. 5, it will be understood that in a typical application, ventricular assist device 100 is coupled to a blood circulatory system within a host patient by suitable blood vessel connections to input coupler 102 and output coupler 104.

Figure 6:
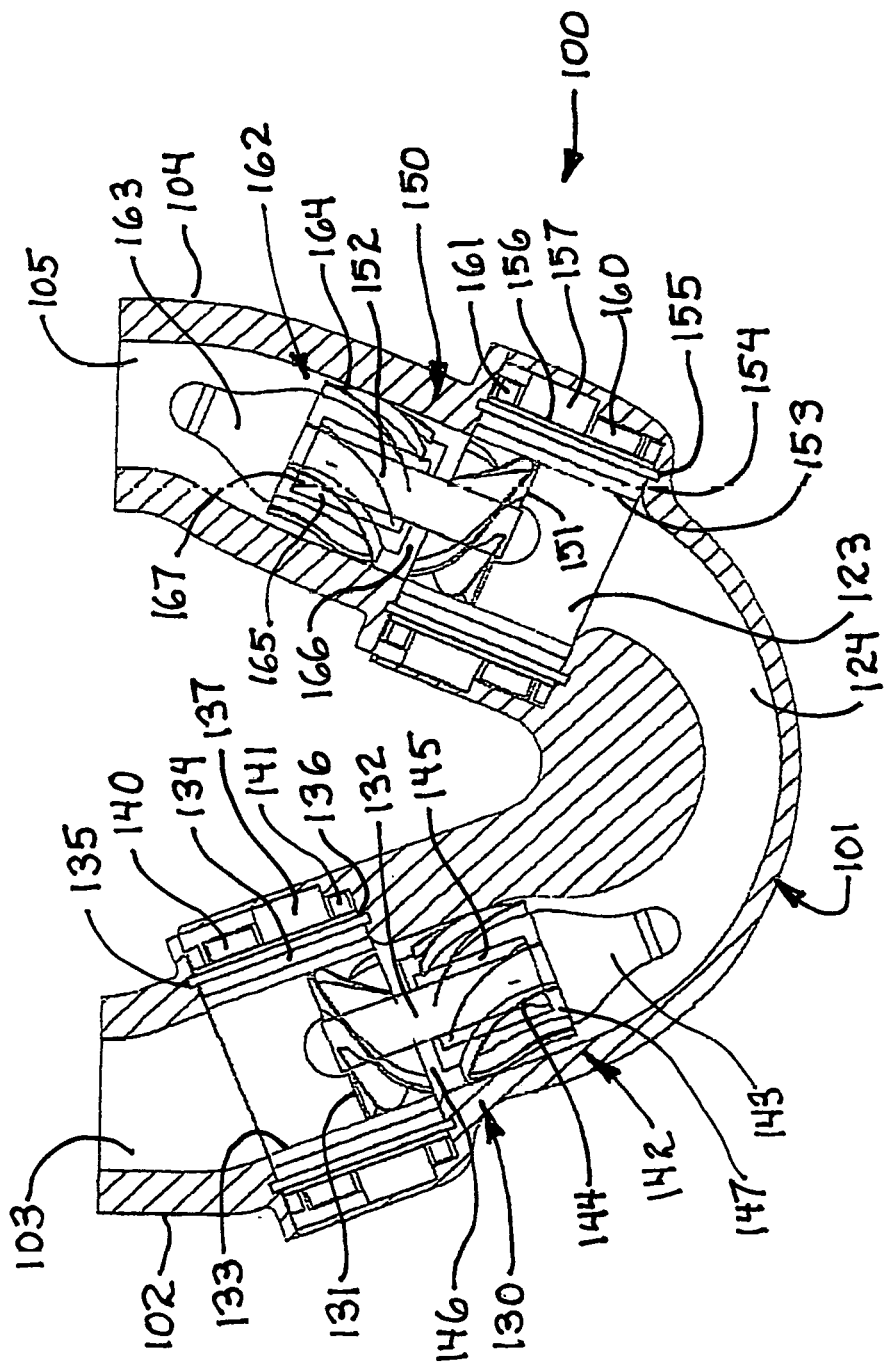
FIG. 6 sets forth a section view of the alternate embodiment of the present invention ventricular assist device shown in FIG. 4.

FIG. 6 sets forth a section view of ventricular assist device 100. As described above ventricular assist device 100 includes a generally U-shaped housing 101 supporting an input coupler 102 and an output coupler 104, respectively. Input coupler 102 further defines an input passage 103 extending through input coupler 102. Correspondingly, output coupler 104 defines an output passage 105 extending through output coupler 104. Housing 101 further defines a pump receptacle 122 within which a turban pump 130 is supported. Housing 101 further defines a pump receptacle 123 within which a turbine pump 150 is supported. Pump receptacles 122 and 123 are coupled by a Venturi passage 124 such that a continuous blood flow passage between input passage 103 of input coupler 102 and output passage 105 of output coupler 104 is formed.

Turbine pump 130 includes a turbine impeller 131 supported upon an arbor 132. Turbine pump 130 further includes a generally cylindrical rotor 133 which is joined to the outer edges of turbine impeller 131 and is therefore rotatable therewith. A cylindrical isolator 135 is preferably formed of a suitable glass material and is fixed to the interior of pump receptacle 122 of housing 101. Isolator 135 is spaced from rotor 133 such that an air gap 134 is formed between rotor 133 and isolator 135. A motor core 136 encloses isolator 135 and is similarly fixed within pump receptacle 122. Turbine pump 130 further includes an outer core ring 137 encircling the outer surface of motor core 136. Turbine pump 130 further includes windings 140 and 141 on either side of outer core ring 137 which similarly encircle motor core 136.

Turbine pump 130 further includes a deswirler 142 having a deswirler body 143 which supports a plurality of curved deswirler vanes 144. Deswirler vanes 144 extend from deswirler body 143 and are fixed within the interior of Venturi passage 124 of housing 101 and secure the position of deswirler 142 therein. Deswirler body 143 further supports a bushing 145 which in turn receives the remaining end of arbor 132. A flared portion 147 is formed between the end of arbor 132 and the end of bushing 145 to provide a thrust load carrying surface which maintains arbor 132 within bushing 145. Arbor 132 is rotatable within bushing 145 such that a bearing is formed therebetween. In the preferred fabrication of the present invention, arbor 132 and bushing 145 are made of a jewel bearing material such as sapphire, or the like.

Turbine pump 150 is virtually identical to turbine pump 130 and thus includes a turbine impeller 151 supported upon an arbor 152. Turbine pump 150 further includes a generally cylindrical rotor 153 which is joined to the outer edges of turbine impeller 151 and is therefore rotatable therewith. A cylindrical isolator 155 is preferably formed of a suitable glass material and is fixed to the interior of pump receptacle 123 of housing 101. Isolator 155 is spaced from rotor 153 such that an air gap 154 is formed between rotor 153 and isolator 155. A motor core 156 encloses isolator 155 and is similarly fixed within pump receptacle 123. Turbine pump 150 further includes an outer core ring 157 encircling the outer surface of motor core 156. Turbine pump 150 further includes windings 160 and 161 on either side of outer core ring 157 which similarly encircle motor core 156.

Turbine pump 150 further includes a deswirler 162 having a deswirler body 163 which supports a plurality of curved deswirler vanes 164. Deswirler vanes 164 extend from deswirler body 163 and are fixed within the interior of pump receptacle 123 of housing 101 and secure the position of deswirler 162 therein. Deswirler body 163 further supports a bushing 165 which in turn receives the remaining end of arbor 152. A flared portion 167 is formed between the end of arbor 152 and the end of bushing 165 to provide a thrust load carrying surface which maintains arbor 152 within bushing 165. Arbor 152 is rotatable within bushing 165 such that a bearing is formed therebetween. In the preferred fabrication of the present invention, arbor 152 and bushing 165 are made of a jewel bearing material such as sapphire, or the like.

In operation, ventricular assist device 100 is positioned within a patient's circulatory system in the manner described in the above-referenced incorporated co-pending patent application utilizing suitable connecting apparatus (not shown) for securing input coupler 102 and output coupler 104 to the patient's blood vessels. As is also described in the above-referenced incorporated co-pending patent application, a power and control system (not shown) is operatively coupled to the electric motor windings within turbine pumps 130 and 150 to provide energizing and control signals for operation of the electric motors therein. As turbine impellers 131 and 151 are caused to rotate, a flow of blood is induced which flows into input passage 103 of input coupler 102 and thereafter through turbine impeller 131 and deswirler 142 through Venturi passage 124 and into pump receptacle 123. This flow continues increased by the rotation of turbine impeller 151 and the resulting blood flow continues outwardly from pump receptacle 123 past deswirler 162 exiting through output passage 105 of output coupler 104. In accordance with an important aspect of the present invention the blood flows induced by the rotations of turbine impellers 131 and 151 immediately flows through the structures of deswirlers 142 and 162 respectively. It will be noted that deswirler vanes 144 of deswirler 142 are oppositely curved with respect to the vanes of turbine impeller 131. This relationship allows deswirler 142 to overcome or straighten the rotational vortex turbulence induced within the blood low as turbine impeller 131 is rotated. This operation is often referred to in the art as "flow straightening". As a result, the blood flow leaving deswirler 142 and entering Venturi passage 124 is substantially free of rotational vortex turbulence. A similar oppositely curved relationship exists between deswirler vanes 164 and turbine impeller 151. Accordingly, deswirler 162 is similarly operative to ensure that the outward blood flow through output passage 105 of output coupler 104 is also substantially free of rotational vortex turbulence.

It has been determined that the size of gap 146 between turbine impeller 131 and deswirler 142 and the size of gap 166 between turbine impeller 151 and deswirler 162 are critical to the proper operation of flow straightening. Accordingly, gaps 146 and 166 are preferably maintained at 0.5 millimeters.

What has been shown is a ventricular assist device having a pair of turbine pumps positioned in a series flow relationship within the blood flow passage of a housing. Each turbine pump is enhanced by a deswirler positioned downstream of the turbine pump impellers. The deswirler acts to reduce or substantially eliminate rotational turbulence or vortex turbulence within the blood flow induced by the rotating turbine impellers.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A ventricular assist device comprising:
   a housing having an input, an output and a coupling passage defining a direction of blood flow from said input, through said coupling passage and out through said output;
   a first turbine pump operative to flow blood from said input, through said coupling passage and through said output;
   a first deswirler positioned downstream of said first turbine pump relative to said direction of blood flow;
   a second turbine pump operative to flow blood from said input, through said coupling passage and through said output;
   a second deswirler positioned downstream of said second turbine pump relative to said direction of blood flow;
   said coupling passage within said housing coupled between said first turbine pump and said second turbine pump and defining a narrowing portion, a venturi portion and an expanding portion.

2. The ventricular assist device set forth in claim 1 wherein said first and said second turbine pumps are arranged in a series blood flow.

3. The ventricular assist device set forth in claim 2 wherein said housing defines a pair of turbine receptacles and wherein said first and second turbine pumps each include:
- a respective turbine receptacle:
- a turbine impeller having a plurality of impeller vanes rotatably supported within said turbine receptacle:
- a magnetic rotor rotatable with and supported by said turbine;
- a deswirler fixed within said turbine receptacle having a plurality of deswirler vanes; and
- a drive coil supported within said housing and encircling said turbine receptacle and said turbine and said magnetic rotor.

4. The ventricular assist device set forth in claim 3 wherein each of said magnetic rotors is cylindrical and defines a respective interior surface and wherein each of said of impeller vanes receives said respective interior surface to join said magnetic rotor to said turbine impeller.

\* \* \* \* \*